US007115092B2

United States Patent
Park et al.

(10) Patent No.: US 7,115,092 B2
(45) Date of Patent: Oct. 3, 2006

(54) TUBULAR COMPLIANT MECHANISMS FOR ULTRASONIC IMAGING SYSTEMS AND INTRAVASCULAR INTERVENTIONAL DEVICES

(75) Inventors: Byong-Ho Park, San Francisco, CA (US); Friedrich B. Prinz, Menlo Park, CA (US); David H. Liang, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 226 days.

(21) Appl. No.: 10/667,230

(22) Filed: Sep. 18, 2003

(65) Prior Publication Data

US 2004/0056751 A1 Mar. 25, 2004

Related U.S. Application Data

(60) Provisional application No. 60/411,924, filed on Sep. 18, 2002.

(51) Int. Cl.
*A61B 1/00* (2006.01)
(52) U.S. Cl. ...................... 600/143; 600/139
(58) Field of Classification Search ................. 600/143
See application file for complete search history.

(56) References Cited

U.S. PATENT DOCUMENTS

| | | | |
|---|---|---|---|
| 4,794,931 A | 1/1989 | Yock | 128/660.03 |
| 4,887,605 A | 12/1989 | Angelsen et al. | 128/660.03 |
| 5,000,185 A | 3/1991 | Yock | 128/662.03 |
| 5,238,005 A | 8/1993 | Imran | 128/772 |
| 5,349,964 A | 9/1994 | Imran et al. | 128/772 |
| 5,373,845 A | 12/1994 | Gardineer et al. | 128/660.09 |
| 5,373,849 A | 12/1994 | Maroney et al. | 128/662.06 |
| 5,377,685 A | 1/1995 | Kazi et al. | 128/662.06 |
| 5,379,772 A | 1/1995 | Imran | 128/662.06 |
| 5,383,923 A | 1/1995 | Webster, Jr. | 607/125 |
| 5,409,000 A | 4/1995 | Imran | 128/642 |
| 5,478,330 A | 12/1995 | Imran et al. | 604/282 |
| 5,482,029 A * | 1/1996 | Sekiguchi et al. | 600/109 |
| 5,606,975 A | 3/1997 | Liang et al. | 128/662.06 |
| 5,779,688 A | 7/1998 | Imran et al. | 604/283 |
| 5,813,997 A | 9/1998 | Imran et al. | 600/585 |
| 5,873,906 A * | 2/1999 | Lau et al. | 128/898 |
| 5,938,623 A | 8/1999 | Quiachon et al. | 600/585 |
| 5,938,671 A | 8/1999 | Katoh et al. | 606/159 |

(Continued)

OTHER PUBLICATIONS

International Search Report of PCT/US03/29517.

*Primary Examiner*—Linda C. M. Dvorak
*Assistant Examiner*—Matthew J. Kasztejna
(74) *Attorney, Agent, or Firm*—Lumen Intellectual Property Services, Inc.

(57) ABSTRACT

A micromanipulator comprising a tubular structure and a structural compliance mechanism that are formed from a tube made of an elastic and/or superelastic material. Fabricated with laser machining and has no mechanical joints, the micromanipulator can be manipulated in various motions and degree-of-freedoms without permanent deformation. Shape Memory Alloys (SMAs) in one embodiment are implemented as main actuators of the micromanipulator. The micromanipulator can be implemented with multiple SMAs to manipulate the mechanism with multiple degree-of-freedom. In another implementation, multiple segments of the mechanisms are formed and arranged in various configurations, including a "double-helix"-like configuration, for enabling intricate motions of the micromanipulator. The micromanipulator is useful for intravascular interventional applications and particularly ultrasonic imaging when coupled with an ultrasound transducer.

48 Claims, 9 Drawing Sheets

U.S. PATENT DOCUMENTS

| | | |
|---|---|---|
| 5,968,064 A | 10/1999 | Selmon et al. .............. 606/189 |
| 6,004,330 A | 12/1999 | Middleman et al. ......... 606/127 |
| 6,110,121 A | 8/2000 | Lenker ....................... 600/463 |
| 6,157,852 A | 12/2000 | Selmon et al. .............. 600/407 |
| 6,200,269 B1 | 3/2001 | Lin et al. .................... 600/466 |
| 6,235,000 B1 | 5/2001 | Milo et al. ............. 604/164.01 |
| 6,241,667 B1 | 6/2001 | Vetter et al. ................ 600/407 |
| 6,241,744 B1 | 6/2001 | Imran et al. ................. 606/159 |
| 6,296,615 B1 | 10/2001 | Brockway ................... 600/486 |
| 6,500,147 B1 | 12/2002 | Omaleki et al. ........ 604/103.09 |
| 6,547,803 B1 | 4/2003 | Seward et al. .............. 606/185 |
| 6,572,551 B1 | 6/2003 | Smith et al. ................ 600/459 |
| 6,599,304 B1 | 7/2003 | Selmon et al. .............. 606/159 |
| 6,749,560 B1 * | 6/2004 | Konstorum et al. ........ 600/143 |

* cited by examiner

FIG. 10

TUBULAR COMPLIANT MECHANISMS FOR ULTRASONIC IMAGING SYSTEMS AND INTRAVASCULAR INTERVENTIONAL DEVICES

CROSS-REFERENCE TO RELATED APPLICATION

This application claims the benefit of a provisional patent application No. 60/411,924, filed Sep. 18, 2002, the entire content and appendices of which are hereby incorporated by reference.

BACKGROUND OF THE INVENTION

1. Field of the Invention

The present invention relates generally to micromanipulators useful for ultrasonic imaging systems and tools, and, more particularly, to a micromanipulator having a tubular structure and at least one compliant mechanism formed from a single tube made of an elastic and/or superelastic material, the micromanipulator enabling treating diseases in a minimally invasive fashion and particularly useful for intravascular intervention applications and the like.

2. Description of the Related Art

Currently, heart disease such as heart attack and stroke is the number one killer in the United States. One out of four men and women would experience this disease during his/her lifetime. In this category, the coronary artery disease is the most serious and often requires an emergency operation to save lives. The main cause of the coronary artery disease is the accumulation of plaques inside artery, which eventually occludes blood vessels. Several solutions are available, e.g., balloon angioplasty, rotational atherectomy, and intravascular stents (balloon-expandable wire mesh implants), to open up the clogged section, which is called stenosis. Traditionally, during the operation, surgeons rely on X-ray fluoroscopic images that are basically planar images showing the external shape of the silhouette of the lumen of blood vessels. Unfortunately, with X-ray fluoroscopic images, there is a great deal of uncertainty about the exact extent and orientation of the atherosclerotic lesions responsible for the occlusion to find the exact location of the stenosis. In addition, though it is known that restenosis can occur at the same place, it is difficult to check the condition inside the vessels after surgery.

In order to resolve these issues, an ultrasonic transducer has been implemented in the endovascular intervention to visualize the inside of the blood vessels. To date, however, the ultrasonic transducer is only able to see side images of the blood vessels by rotating the transducers in parallel to the blood vessels. Thus, known ultrasonic transducers have a fundamental limitation in their uses in endovascular/intravascular applications. What is needed is a micromanipulator capable of maneuvering the ultrasonic transducer and generating a scanning motion so that front images of the blood vessels in various angles can be captured.

SUMMARY OF THE INVENTION

The present invention addresses this need in the art by disclosing a new micromanipulator useful for ultrasonic imaging, intravascular intervention, and the like. The micromanipulator enables its user to visualize and inspect inside blood vessels in essentially all directions and to treat any abnormalities identified in a minimally invasive manner.

According to an aspect of the present invention, an elastic or superelastic material is utilized as a structural material for the new micromanipulator. Elasticity or superelasticity is therefore a key design parameter for compliant mechanisms of the micromanipulator. In principle, when a compliant mechanism is deformed with an actuator, strain energy is stored inside the underlying structure during deformation (elastic and plastic). The stored energy is then directly utilized to produce a bias force to return the structure to its original shape.

In some embodiments, Shape Memory Alloys (SMAs) are implemented as main actuators for the micromanipulator. The compliant mechanism is actuated with SMA contraction as well as rotation motion to maximize output displacement. By activating the SMAs, it is possible to achieve ±30° angular deflections. It is anticipated that the compliant mechanism can be designed to accommodate two other SMAs in an orthogonal direction, in which case, the compliant mechanism can be manipulated with two degree-of-freedom, which would provide the micromanipulator with full 3-D scanning motions.

According to an aspect of the invention, a Nd:YAG laser is implemented in the fabrication of the compliant structure out of a tube. A tubular nitinol structure with compliant mechanism was successfully fabricated using laser machining with a laser beam size of about 30 µm. The outer diameter of the tube is about 800 µm and the wall thickness is about 75 µm. Actual feature size is about 25 µm, which is mostly limited by the size of the laser beam. Thus, by reducing the beam size, resolution of the laser machining can be enhanced.

Micromanipulators of the present invention with novel features such as structural compliance, elasticity/superelasticity, tubular structure, etc. are particularly useful in the fields of intravascular ultrasound (WUS) imaging and intravascular intervention.

Still further objects and advantages of the present invention will become apparent to one of ordinary skill in the art upon reading and understanding the drawings and detailed description of the preferred embodiments disclosed herein. As it will be appreciated by one of ordinary skill in the art, various changes, substitutions, and alternations can be made without departing from the principles and the scope of the present invention. As such, the drawings disclosed herein are for purposes of illustrating embodiments of the present invention and are not to be construed as limiting the present invention.

DETAILED DESCRIPTION

To address the fracture toughness and stress issue, a superelastic material such as nitinol is utilized as a structural material for the micromanipulator of the present invention. Thus, superelasticity is implemented as a key design parameter for compliant mechanisms disclosed herein. In principle, when a compliant mechanism is deformed with an actuator, strain energy is stored inside the underlying structure during deformation (elastic and plastic). The stored energy is then directly utilized to produce a bias force to return the structure back to its original shape. However, an elastic material such as stainless steel can also be utilized as a structural material for compliant mechanisms if the fracture and stress issue can be appropriately addressed with elasticity as a design parameter.

Figure 1:
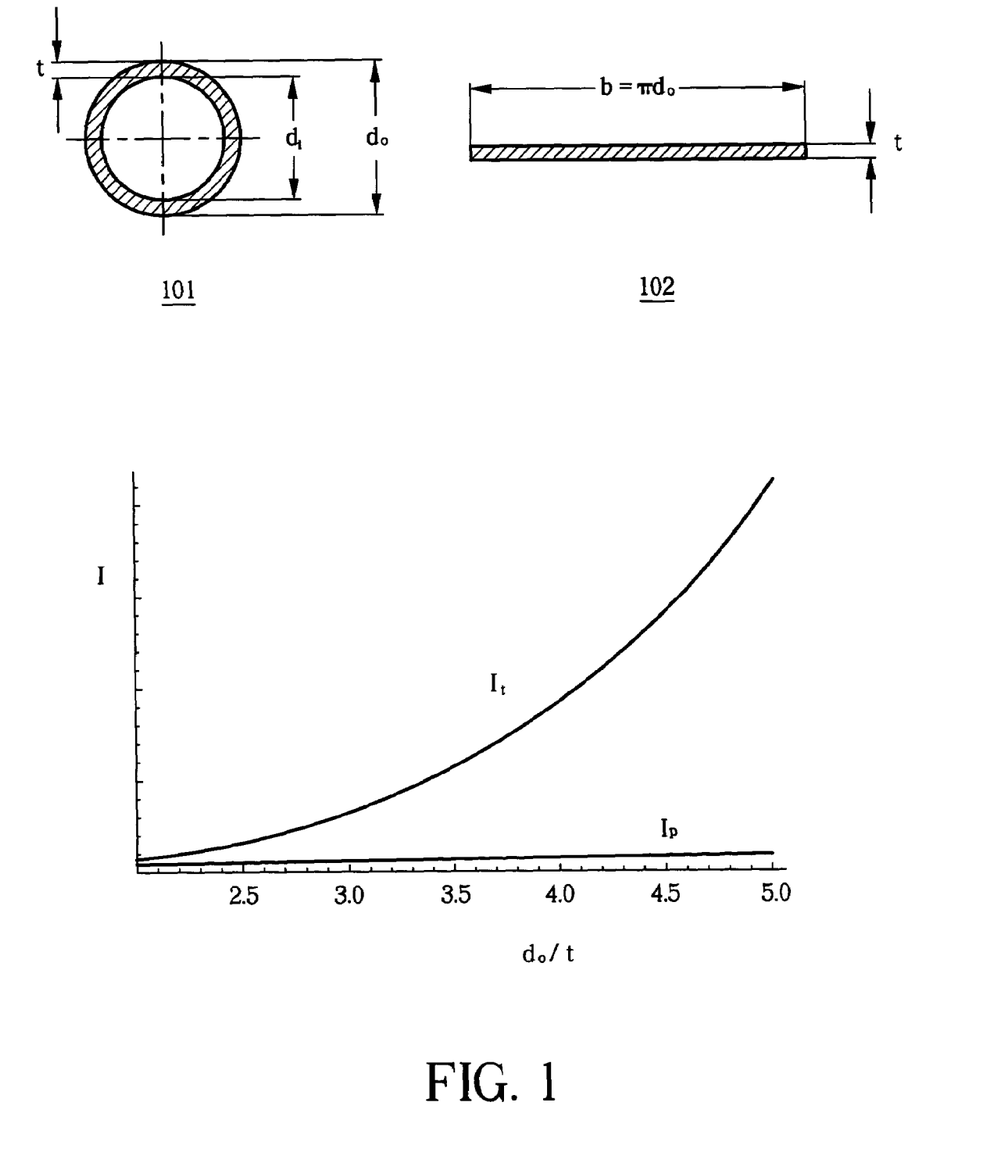
FIG. 1 compares the second moment of inertia between a plate form and a tubular structure.

To shape a nitinol structure, there are two fabrication processes currently commercially available: chemical etching and laser machining. However, these two processes are not able to precisely control etching depth. Thus, it is very difficult to have a variation in thickness and, consequently, the thickness of the mechanism determines the substrate thickness. This presents another issue in design, which is structural rigidity. For instance, if the substrate thickness is on the order of tens of microns, the supporting structure also starts deflecting as the mechanism moves. This deflection at the supporting structure, which is supposed to be fixed, directly contributes to loss of output displacement. Structural rigidity is mostly a shape factor, which is related to flexural modulus, EI. Considering the structural rigidity, a tube shape 101 is more attractive than a plate form 102 as demonstrated in FIG. 1, where $$I_P = \frac{bt^3}{12} = \frac{\pi d_o t^3}{12} \quad (1)$$

$$I_t = \frac{\pi(d_o^4 - d_i^4)}{64} = \frac{\pi(d_o^4 - (d_o - 2t)^4)}{64} \quad (2)$$

$I_t$ and $I_p$ respectively represents the second moment of inertia of a tube and a plate. The lengths of the plate and the tube are assumed to be the same for correct comparisons in equations (1) and (2).

Figure 2A:
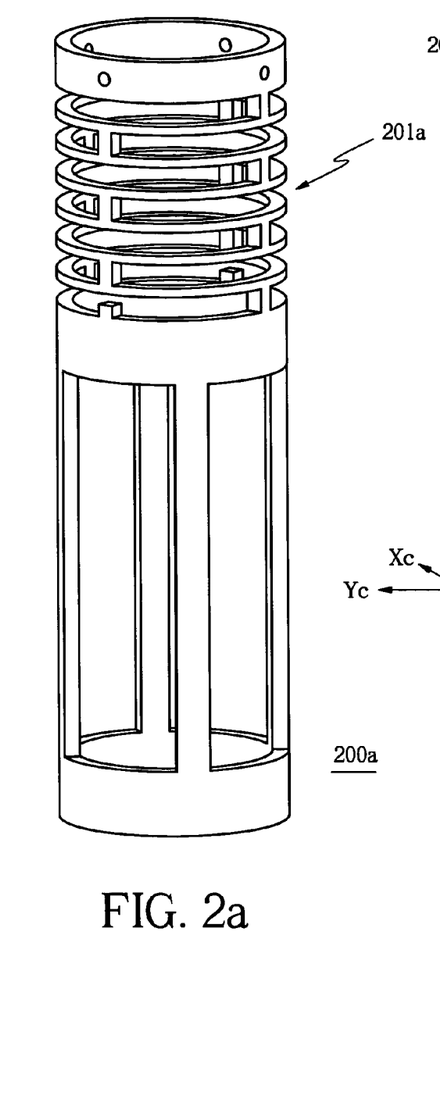
FIGS. 2A–2B show two tubular structures each with a built-in compliant mechanism in different design configuration.
Figure 2B:
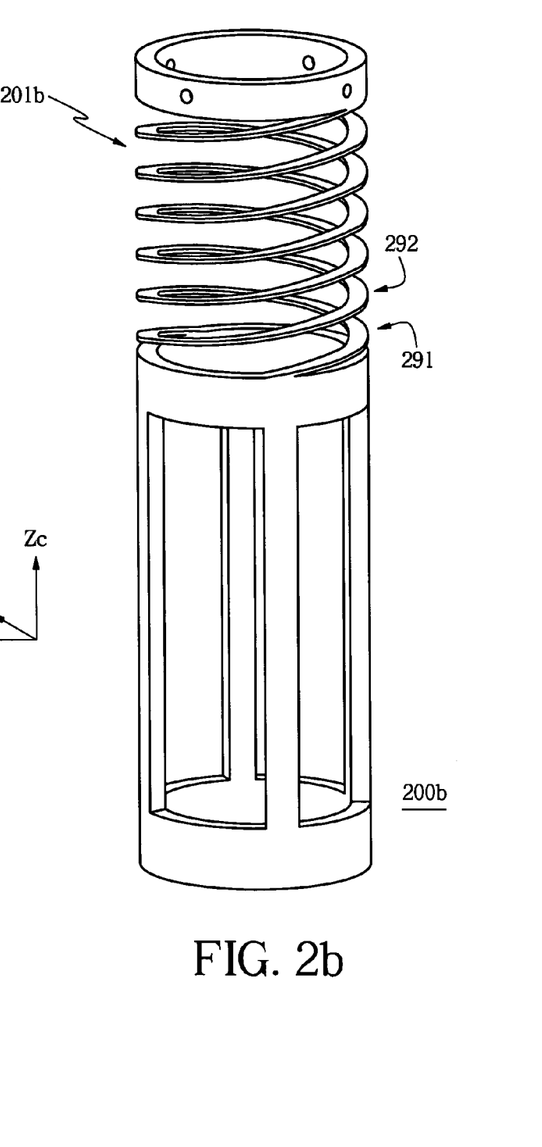

FIG. 1 shows that there is an exponential difference in structural rigidity as $d_o/t$ increases, which is a reasonable estimation for the compliant mechanism. Thus, the tube was selected as a basic form of structure for the compliant mechanisms. FIG. 2A illustrates an exemplary tubular structure 200a with a built-in compliant mechanism 201a. FIG. 2B illustrates another exemplary tubular structure 200b with a built-in compliant mechanism 201b in a helical configuration having helix 291 and helix 292 intertwined in a "double helix"-like fashion. The mechanism design can be any shape and/or configuration as long as it utilizes structural compliance (elasticity and/or superelasticity) as a main design parameter. Similarly, as one skilled in the art would appreciate, the rest of the tubular structure can be in any suitable configuration, size, and length, etc., optimized for a particular application and thus is not limited to what is shown here. Moreover, in addition to nitinol, other flexible, resilient biocompatible metal or polymer materials can also be utilized as long as they have reversible structural behaviors, i.e., have elastic and/or superelastic behaviors while actuated.

As illustrated in FIG. 2B, compliant mechanisms can be in a "double helix" configuration. It is desirable with the present invention that any bending strain of the compliant mechanisms is distributed substantially evenly along their entire lengths. This reduces peak strain, which in various embodiments, can be, 4% or less, 3% or less, 2% or less and 1% or less. The "double helix" configuration provides greater symmetry in motion and provides a more even bending. It is desired that the stiffness of compliant mechanisms in different directions be substantially the same.

In various embodiments, the elastic bending strength of the compliant mechanisms is customized in order to match with that of the actuators. In some embodiments, the actuators have slightly stiffer elastic bending strengths than those of the compliant mechanisms. In one embodiment, the compliant mechanisms are stiffer than the actuators when the actuators are relaxed, and the compliant mechanisms are softer than the actuators when the actuators are active. It is desirable to provide compliant mechanisms in configurations, such as those of the "double helix" configurations, that have as little stress concentration as possible.

According to the present invention, the strain of a compliant mechanism is distributed, while minimizing the occurrence of strain location. The mechanical characterization of a compliant mechanism can be tuned by modifications in, (i) stiffness, (ii) peak strain (maximum strain), (iii) size, (iv) fatigue life, and the like. In one embodiment, the upper limit of strain is no more than 4%. The bending stiffness depends on actual application. By way of illustration, and without limitation, the bending stiffness of a compliant mechanism can be at least 0.5 N-mm and no more than 10 N-mm. In various embodiments, compliant mechanisms are stiffer than the imaging device. The associated actuators are also stiffer than the imaging device. The actuators need a longer thermal time constant than the imagining device.

Figure 3:
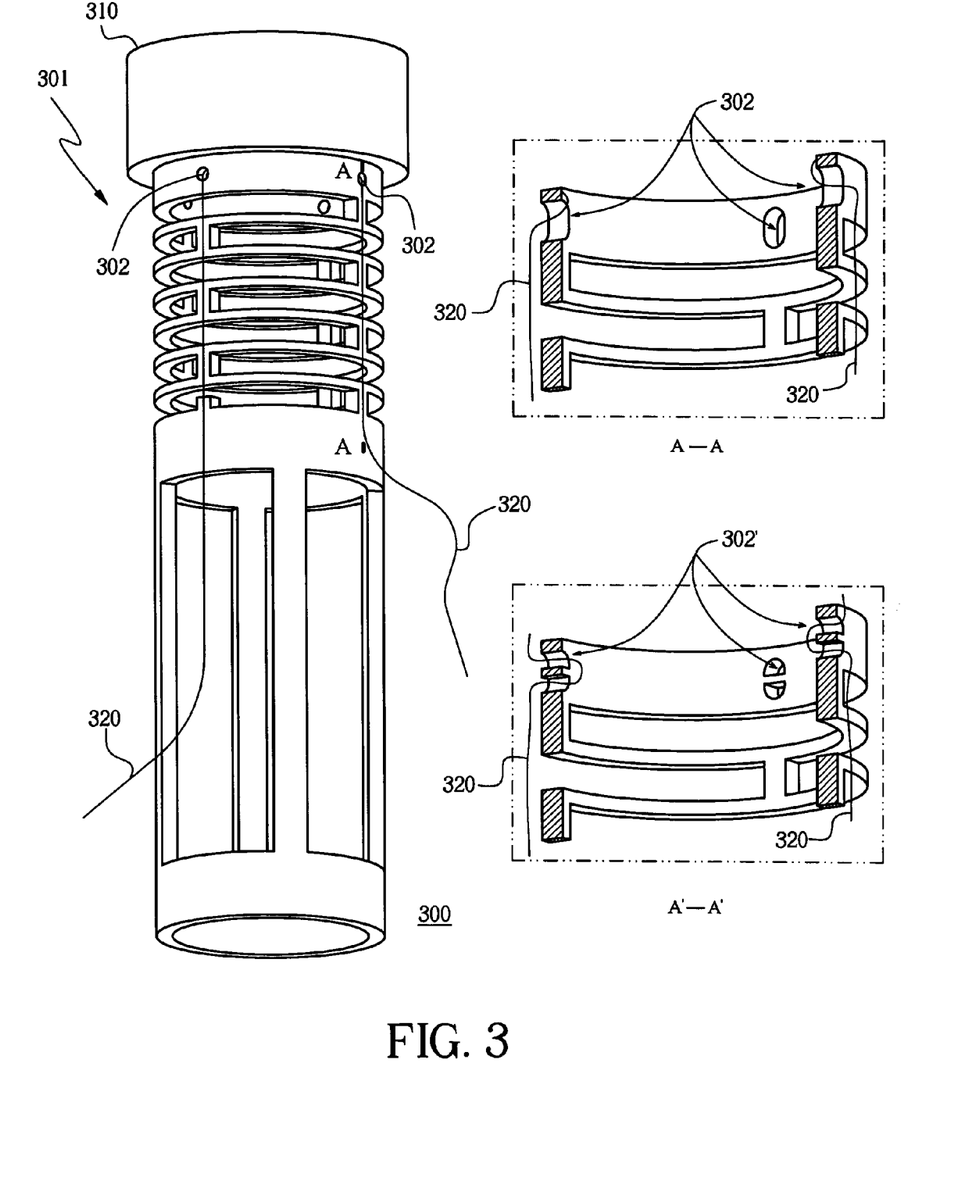
FIG. 3 schematically shows an ultrasound transducer coupled to a micromanipulator having the compliant structure of FIG. 2A and two SMA actuators configured to actuate the compliant mechanism thereof.

FIG. 3 schematically shows, according to an aspect of the invention, a micromanipulator 300 tightly coupled with an ultrasound transducer 310 for image scanning. Micromanipulator 300, as well as the other embodiments of micromanipulators disclosed herein, provide for steering, viewing and treatment at sites within vessels of the body, as well as for industrial applications. As discussed before, most of the research efforts on ultrasonic imaging system for intravascular intervention utilized ultrasonic transducers to inspect sidewall images inside blood vessels. These transducers are turned inside at high speed to capture the inner images, which do not provide any information about the front images. As one skilled in the art would appreciate, it would be extremely helpful if cardiologists can see the cross-section (front images) of the blood vessels in front of the device used to remove the stenosis. To catch the front images in various angles needed to create the images in front of the device, a micromanipulator is required to maneuver the transducer and generate a scanning motion.

The micromanipulator 300 enables the ultrasound transducer 310 to be directly coupled to the compliant mechanisms 301. In this fashion, the rotational center of the transducer 310 for the scanning motion is substantially closer to the rotational axis of the mechanisms 301. This novel configuration can produce images with much better resolutions than known devices. In an embodiment, SMAs (Shape Memory Alloys) are implemented as main actuators 320 for the micromanipulator 300. To allow the SMAs 320 be attached thereto, the micromanipulator 300 might have one or more attachment points or built-in micro structures such as welding-enabling structures 302 as shown in a cross-sectional view A—A and clamping-enabling structures 302' as shown in another cross-sectional view A'—A'. In some embodiments, the SMAs 320 are attached to the compliant apparatus via the one or more attachment points or welding-enabling structure 302 using a laser having a laser beam size of about 200 µm or less. In some embodiments, the SMAs 320 are fastened to the compliant apparatus via the built-in clamping-enabling structures 302'.

The compliant mechanisms 301 are actuated with SMA 320 actuators based on shape memory effects including contraction as well as rotation motion to maximize output displacement. As one skilled in the art can appreciate, the SMA actuators can be in any shape such as wire, spring, coil, etc. and thus is not limited to what is shown here.

The amount of continuous power applied to all of the actuators is 1 W or less, with a peak power of 10 W or less. It will be appreciated that the micromanipulator of the present invention can have at least two actuators. Additional actuators can be utilized, subject to the ability to manufacture, cost, size, and like.

Figure 4:
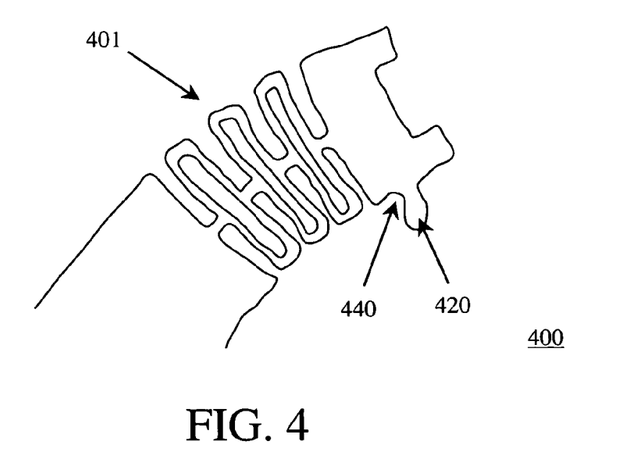
FIG. 4 is a line drawing showing an exemplary compliant structure of FIG. 2A having no mechanical joints and made of a nitinol tube with a built-in compliant mechanism.

According to an aspect of the invention, a Nd:YAG laser was implemented in fabricating compliant structures out of nitinol tubes. The laser has a wavelength of 1.06 µm and an average power of 75W. The cutting depth of the laser is about 125 µm. Nd:YAG lasers as well as other lasers suitable for the laser machining are known in the art and thus are not further described herein. Referring to FIG. 4, a compliant structure 400 was successfully fabricated out of a nitinol tube using laser machining. The outer diameter of the nitinol tube is about 800 µm and the wall thickness is about 75 µm. The compliant structure 400 can be characterized as a tubular nitinol structure with a built-in compliant mechanism 401 and loading points 440. The compliant structure 400 shown in FIG. 4 is actuated with a SMA actuator 420 via one of the loading points 440. It is also useful to pattern the compliant structures with holding structures (not shown) for temporarily holding the SMA actuator during assembly and to decrease stress upon the SMA actuator at the attachment point in the final device. In this embodiment, the compliant structure 400 has features about 30 µm in size. In practice, actual feature size is mostly limited by the size of the laser beam, which was about 25 µm in this example. It will be apparent to one skilled in the art that, by reducing the beam size, the resolution of the laser machining can be enhanced.

The size of the various elements of micromanipulators of the present invention can be customized depending on applications. For example, if it is desired to insert a micromanipulator into the inner diameter of another device, the diameter of the micromanipulator is selected so that the micromanipulator can fit in the inner diameter of that device. In a more specific example, for a coronary artery, it is desired to have a micromanipulator with a diameter of 2 mm or less. For larger vessels, the diameter of micromanipulator can be 4 mm or less.

The tubular nitinol compliant structure 400 was tested under cyclic loading. Specifically, SMA actuators generated a cyclic motion of the compliant structure 400 at 10 Hz under water. The compliant structure 400 successfully endured the mechanical loading test while it was actuated. No mechanical failure was noticed up to 20,000 cycles.

Figure 5A:
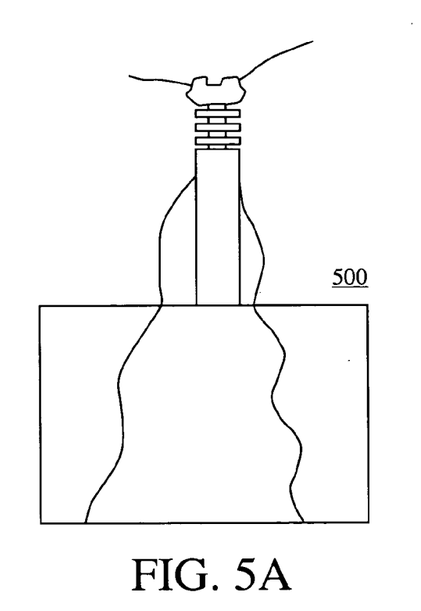
FIGS. 5A–5B are line drawings showing a micromanipulator having the compliant structure of FIG. 4 and two SMA actuators configured to actuate the compliant mechanism thereof.
Figure 5B:
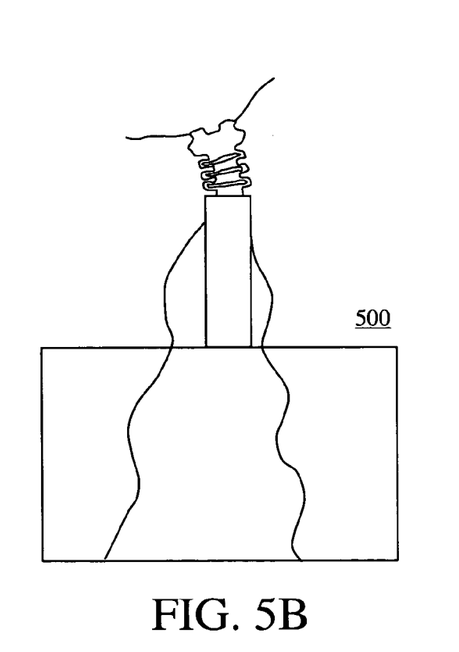

FIGS. 5A–5B show a micromanipulator 500 having a compliant structure as shown in FIG. 4 and two main actuators in the form of SMA wires successfully assembled therewith. In various embodiments, the actuators of micromanipulator 500 provide angular deflection of at least ±20°. In the embodiments illustrated in FIGS. 5A–5B the actuators are activated, resulting in ±40° angular deflections. The micromanipulator 500 can be assembled with two other actuators in an orthogonal direction. The micromanipulator 500 so assembled will be able to manipulate the compliant mechanism with two degree-of-freedom, which would provide full 3-D scanning motions. 3-D scanning motions can be achieved by utilizing an actuator for one direction of deflection, and then a second actuator for the second direction of deflection. It will be appreciated that the second direction of deflection can be achieved by rotation movement, for example by way of illustration, and without limitation, in a helical type of scan.

Figure 6:
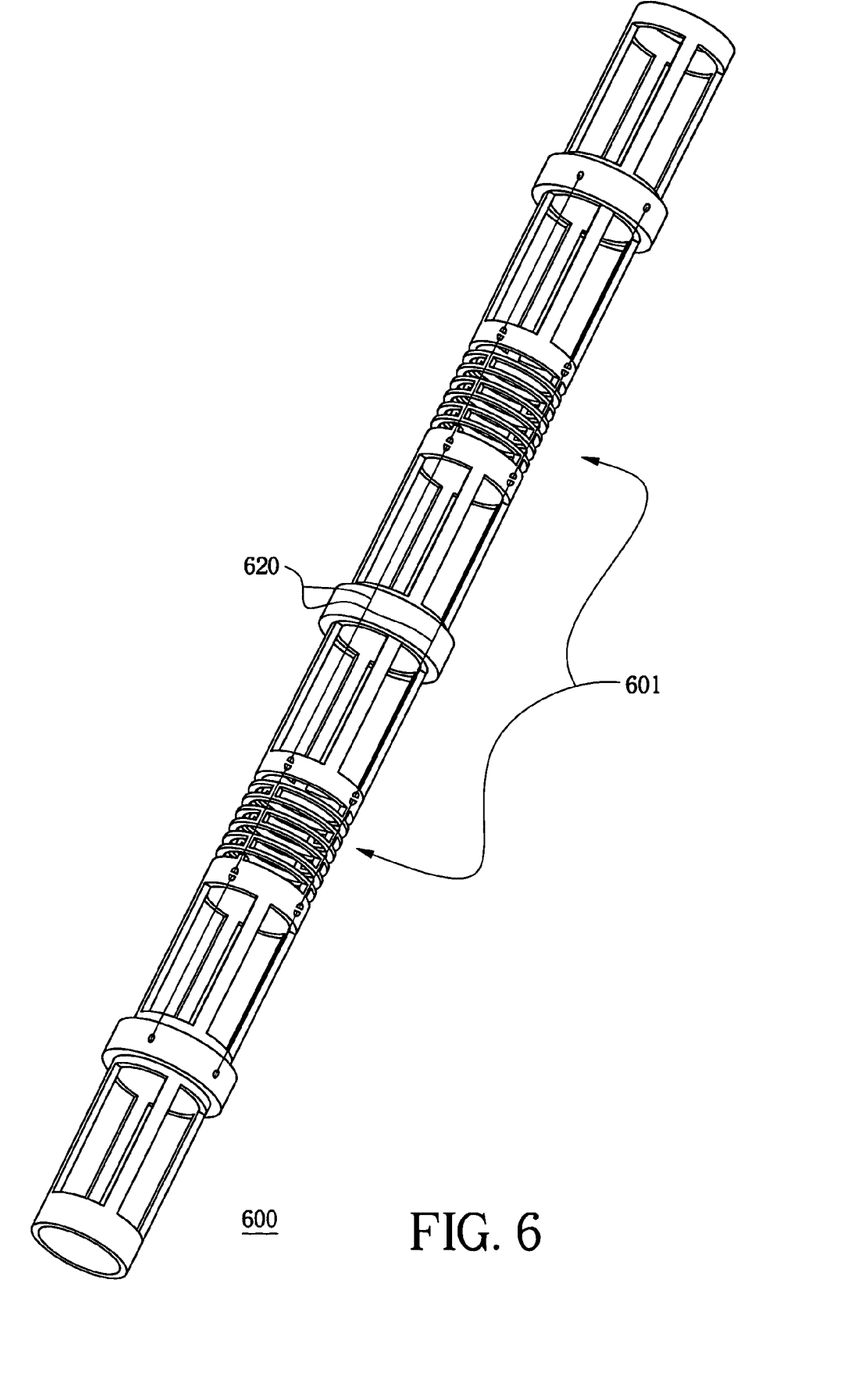
FIG. 6 schematically shows an implementation of FIG. 2A useful for a catheter steering system. The tubular compliant structure has multiple segments of compliant mechanisms each individually controllable via SMA actuators assembled therewith.

In addition to being particularly useful in ultrasound intravascular interventional devices, systems, and applications, the present invention can also be useful in catheter steering related applications including but not limited to any vessels in the body, such as those in neurology, biliary vessels, the fallopian tubes, coronary vessels (including peripheral vessels), and the like. It will be appreciated that the present invention can also be utilized for industrial applications as mentioned above. In a conventional catheter steering system, it is difficult to steer a small catheter inside human blood vessels, especially in a small artery. However, by implementing a compliant structure with multiple segments of compliant mechanisms in various configurations and individually controlling each segment, it is possible to generate intricate motions and steer the catheter in any direction, even in a tiny area. For example, a catheter steering system implementing a micromanipulator 600 according to the present invention may include multiple segments of compliant mechanisms 601 actuated with SMAs 620, as shown in FIG. 6. These tubular compliant mechanisms are arranged in various configurations for intricate motions of the micromanipulator. Such catheter steering system is particularly useful for intravascular applications including imaging and therapy.

Figure 7:
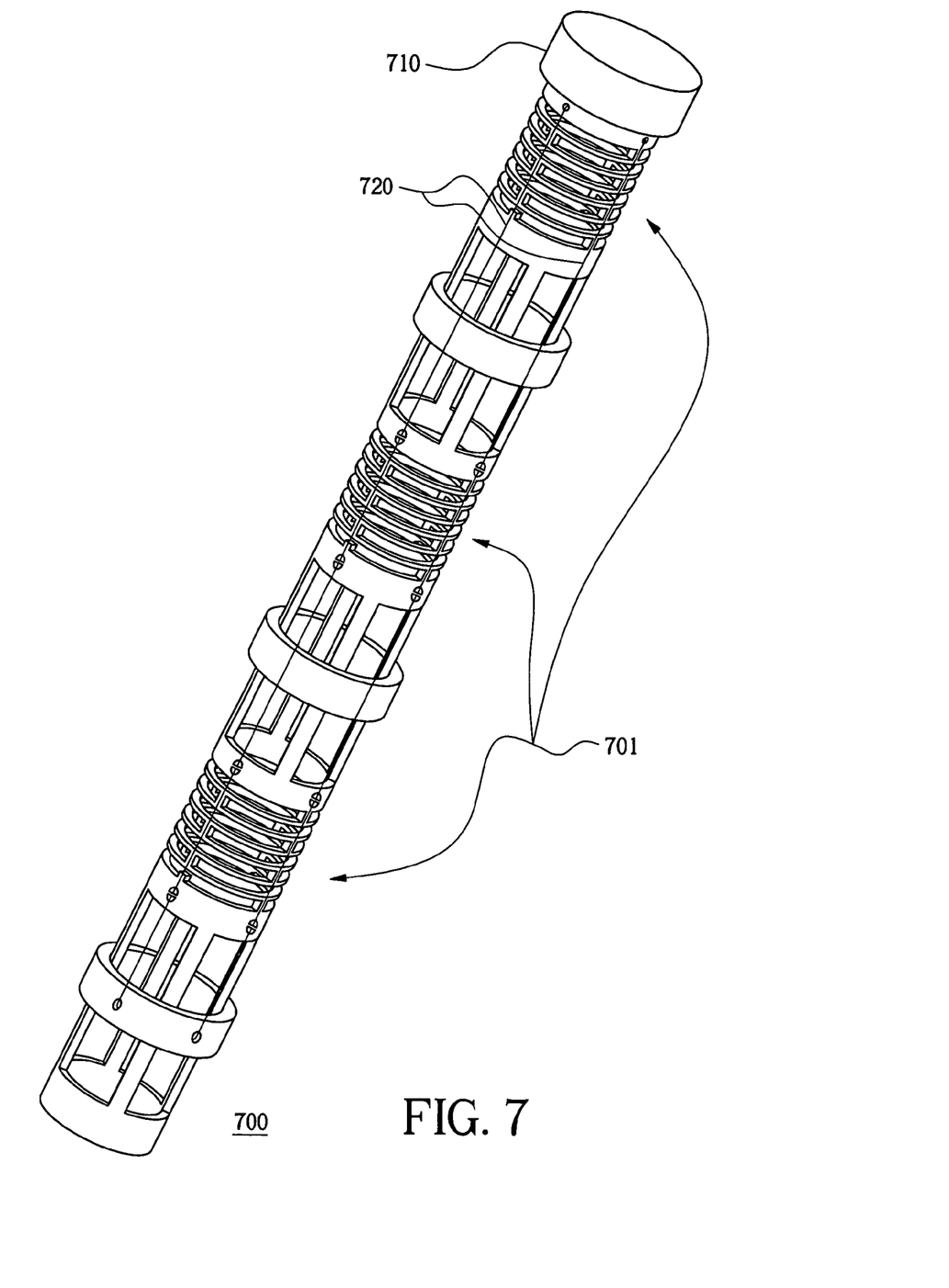
FIG. 7 schematically shows an implementation of FIG. 6 coupled with an ultrasound transducer.

FIG. 7 shows a micromanipulator 700 with an ultrasound transducer 710 directly coupled thereto at one end of the micromanipulator 700 for forward imaging. The micromanipulator 700 has multiple segments of compliant mechanisms 701 actuated with SMAs 720. Multiple segments of compliant mechanisms 701 are useful for vessels with different curvatures. For example, one section of a vessel may require a larger curvature than another area. Therefore, multiple segments of compliant mechanisms 701 make it easier to traverse through a vessel with different curvatures. A user of the system controls individual segment's compliant mechanism via a user interface of an external electronic circuitry, e.g., a computer (not shown).

Figure 8:
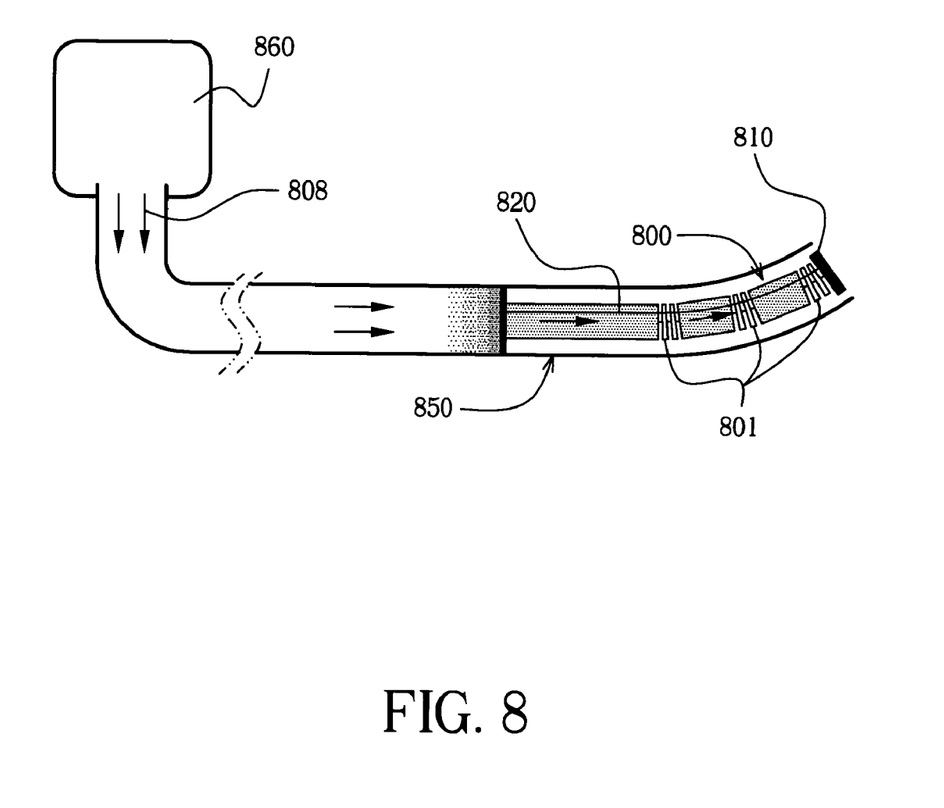
FIG. 8 schematically shows an exemplary intravascular imaging device embodying the implementation of FIG. 7, the imaging device integrated with a cooling system.

When SMAs are implemented as main actuators for the micromanipulator, the performance (e.g., bandwidth and endurance) of the manipulator and devices associated therewith, e.g., an imaging or therapeutic device, can be substantially enhanced by regulating the temperature of the SMAs. Regulation of the temperature can be controlled by any suitable cooling system (e.g., peristaltic pump and IV pump). FIG. 8 shows a micromanipulator 800 having multiple segments of compliant mechanisms 801 actuated by SMAs 820. The micromanipulator 800 is coupled to an ultrasound transducer 810 and steered by SMA actuators 820. A plastic tube, catheter 850, encapsulates the micromanipulator 800, SMAs 820, transducer 810, etc. A cooling system 860, comprising a pumping means and cooling fluid, provides a constant fluid flow 808 to the micromanipulator 800 to prevent the SMAs 820 from overheating during normal operation. Here, the cooling fluid can be any biocompatible solution such as water or saline.

Figure 9:
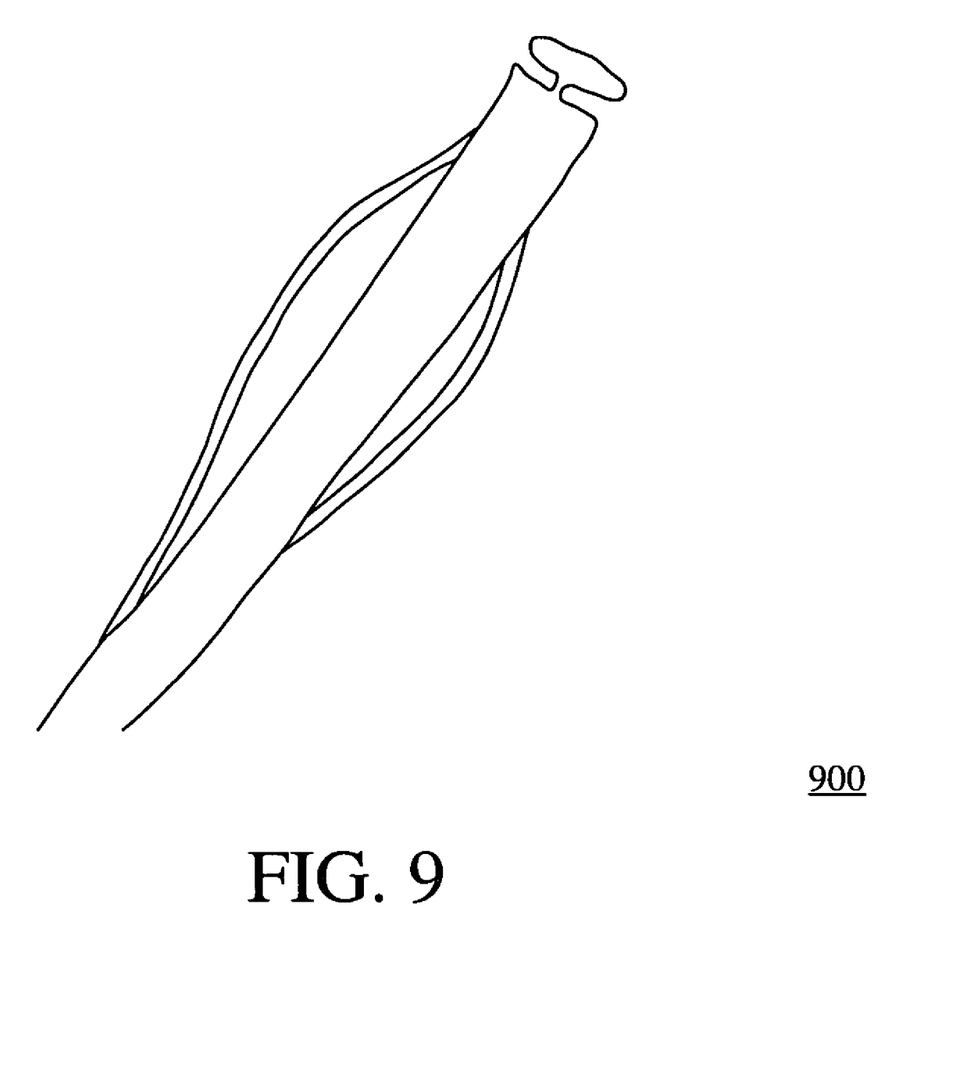
FIG. 9 is a line drawing showing another exemplary compliant structure under loading in a bulging-out configuration.
Figure 10:
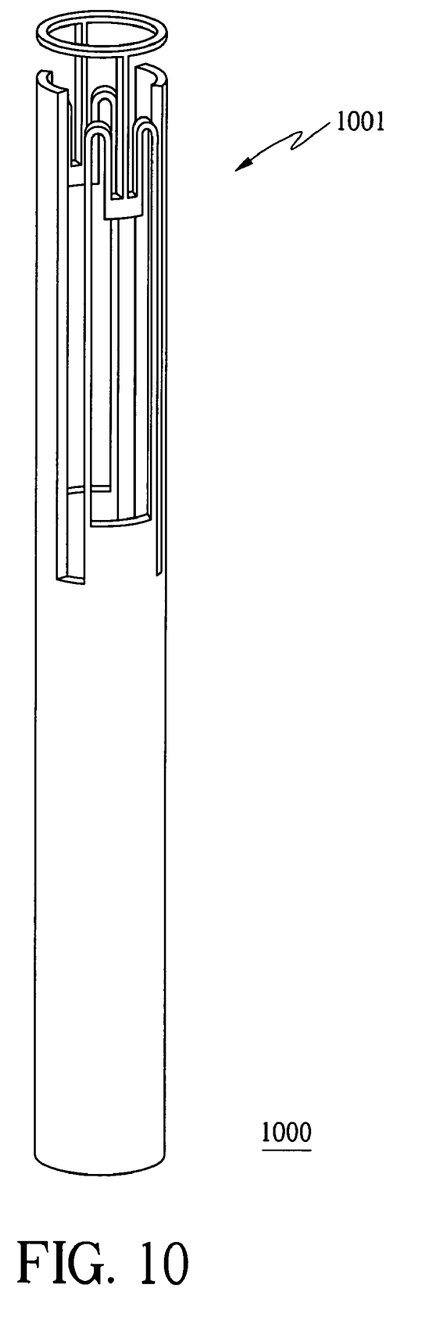
FIG. 10 schematically shows a tubular structure with a built-in compliant mechanism that enables the bulging-out configuration of FIG. 9.

Another application includes utilizing the novel design disclosed herein for angioplasty. Currently, depending on the size of arteries that need to be cleared, surgeons use different sizes of balloons during operation. This means that they would have to change balloon sizes several times and each balloon must be taken out of the body for another balloon to be inserted in. As one skilled in the art would appreciate, the exchange of balloons is a necessary but undesirable procedure. Implementing the compliant mechanisms disclosed herein, it is possible to cover certain ranges of balloon sizes with one single device, as exemplified in FIG. 9. FIG. 9 shows an actual compliant structure 900 under loading in a bulging-out configuration. FIG. 10 schematically shows a tubular structure 1000 with a built-in compliant mechanism 1001 that enables the bulging-out configuration of FIG. 9. It will be apparent to one skilled in the art that the compliant mechanisms disclosed herein have more capabilities in terms of pressure and deployment control than prior art surgical balloons. Moreover, with the present invention, the need to exchange balloons during operation can be substantially reduced or eliminated, thereby simplifying and possibly shorting the angioplasty procedure, making it easier on the surgeons and safer for the patients. The advantages of the present invention are innumerable.

To date, we are not aware of any methods for manufacturing compliant mechanisms out of a nitinol tube for intravascular intervention. Similarly, we are not aware of anyone implementing laser machining as a main fabrication tool for constructing compliant mechanisms. The present invention advantageously utilizes structural compliance, elasticity/superelasticity, and strain energy as a restoring force. Compliant structures and micromanipulators based on these features (structural compliance, elasticity/superelasticity, tubular structure, etc.) as disclosed herein are believed to be unprecedented. The present invention is useful in many fields, e.g., a micromanipulator implemented with an ultrasound transducer such as one shown in FIG. 3 would be useful in intravascular ultrasound (IVUS) applications and particularly in forward imaging systems. A micromanipulator implemented with multiple segments of compliant mechanisms would be useful in steering a catheter in any direction, even in a tiny area. In various embodiments, the present invention can utilize a variety of different interventions for treatment, including but not limited to laser, rotor blader, RF, mechanical, stiff guide wire, microwave, ultrasound, chemical, and the like.

A micromanipulator implemented with a bulging-out configuration as shown in FIGS. 9–10 would be useful in angioplasty and other types of operations where exchanging different sizes of balloons and the like is necessary but undesirable. The micromanipulator of the present invention is made of a monolithic material, e.g., a nitinol tube with a reversible structural behavior, with a built-in compliant mechanism. Since there are no mechanical joints, the micromanipulator can be very small and can facilitate surgical operations in a minimally invasive fashion.

Although the present invention and its advantages have been described in detail, it should be understood that the present invention is not limited to or defined by what is shown or described herein. Known methods, systems, or components may be discussed without giving details, so to avoid obscuring the principles of the invention. As it will be appreciated by one of ordinary skill in the art, various changes, substitutions, and alternations could be made or otherwise implemented without departing from the principles of the present invention. As such, the drawings are for purposes of illustrating a preferred embodiment(s) of the present invention and are not to be construed as limiting the present invention. Accordingly, the scope of the invention should be determined by the following claims and their legal equivalents.

We claim:

1. A compliant apparatus comprising:
   a tubular structure made of elastic or superelastic material, said tubular structure defining an axis, and
   at least one compliant mechanism integrally formed from a portion of said tubular structure by symmetrically removing material from the tubular structure with respect to the axis, thereby forming symmetrical bending segments that are symmetrical in cross section with respect to the axis, without forming mechanical joints;
   wherein each symmetrical bending segment of the compliant mechanism is capable of being controlled to bend away from the axis in a first direction and in an opposite, second direction, with substantially the same degree of strain, and
   without permanent deformation.

2. The compliant apparatus of claim 1, wherein the cross-section of the tube is characterized as circular, oval, rectangular, square, straight, curvy, angular, or irregular.

3. The compliant apparatus of claim 1, wherein the material is selected from the group consisting of an elastic alloy including stainless steel and titanium alloy, and a superelastic alloy including nitinol, Cu—Al—Ni, Cu—Al, Cu—Zn—Al, Ti—V and Ti—Nb alloy.

4. The compliant apparatus of claim 1, wherein the compliant mechanism stores strain energy and utilizes the stored energy as a bias force for shape recovery.

5. The compliant apparatus of claim 1, further comprising at least one actuators.

6. The compliant apparatus of claim 5, wherein the at least one actuators are made of Shape Memory Alloys (SMAs) and wherein the SMAs are based on shape memory effects including contraction, rotation, and a combination thereof.

7. The compliant apparatus of claim 6, wherein the SMAs are configured for manipulating the compliant apparatus and the compliant mechanism.

8. The compliant apparatus of claim 5, wherein the at least one actuators are characterized as piezoelectric or electroactive polymer actuators.

9. The compliant apparatus of claim 5, wherein the at least one actuators are characterized as wires connected to an external apparatus and actuated remotely via the external apparatus.

10. The compliant apparatus of claim 5, wherein the at least one actuators are characterized as Shape Memory Alloy wires or Shape Memory Alloy springs.

11. A method of fabricating the compliant apparatus of claim 1, comprising:
forming the compliant mechanism and the tubular structure out of a tube with laser machining.

12. The method of claim 11, wherein
the laser machining has a laser beam size of about 50 µm or less.

13. The compliant apparatus of claim 1, further comprising at least one built-in micro structure selected from the group consisting of a welding-enabling structure and a clamping-enabling structure.

14. A method of joining the compliant apparatus of claim 13 with at least one actuator, comprising the step of:
attaching the at least one actuator to the compliant apparatus via the at least one built-in micro structure.

15. The method of claim 14, wherein the at least one built-in micro structure is the welding-enabling structure, the method further comprising the step of:
welding the at least one actuator to the welding-enabling structure using a laser.

16. The method of claim 15, wherein
the laser has a laser beam size of about 200 µm or less.

17. An ultrasonic imaging system useful for intravascular ultrasound forward imaging applications, the ultrasonic imaging system comprising:
a compliant apparatus sized for intravascular use, having no mechanical joints and capable of being manipulated through at least one degree of freedom without permanent deformation, the compliant apparatus comprising:
a tubular structure having an axis and formed from a tube made of a material having a reversible structural behavior;
at least one compliant mechanism integrally formed from the tube by removing material from the tube to facilitate bending motion;
a forward-looking ultrasound transducer coupled to the compliant apparatus; and
at least one force-generating actuators attached to and located with the compliant apparatus for manipulating the compliant apparatus by bending the at least one compliant mechanism away from the axis.

18. The ultrasonic imaging system of claim 17, wherein the reversible structural behavior is characterized as elastic or superelastic.

19. The ultrasonic imaging system of claim 17, wherein the material is selected from the group consisting of an elastic alloy including stainless steel and titanium alloy, and a superelastic alloy including nitinol, Cu—Al—Ni, Cu—Al, Cu—Zn—Al, Ti—V and Ti—Nb alloy.

20. The ultrasonic imaging system of claim 17, wherein the at least one actuators are made of Shape Memory Alloys (SMAs) and wherein the SMAs are based on shape memory effects including contraction, rotation, and a combination thereof to maximize output displacement of the at least one compliant mechanism.

21. The ultrasonic imaging system of claim 17, wherein the at least one actuators are characterized as piezoelectric or electroactive polymer actuators.

22. The ultrasonic imaging system of claim 17, wherein the at least one actuators are characterized as wires connected to an external apparatus and actuated remotely via the external apparatus.

23. The ultrasonic imaging system of claim 17, further comprising:
two additional actuators configured to actuate the compliant apparatus in an orthogonal direction, enabling the compliant apparatus to provide the ultrasound transducer with full three dimensional scanning motions.

24. The ultrasonic imaging system of claim 23, wherein the at least one actuators and the two additional actuators are characterized as SMA wires or SMA springs.

25. A micromanipulator comprising:
a tubular elastic or superelastic element having an axis, having no mechanical joints, and formed from a tube made of a material having a reversible structural behavior by removing material from the tubular element to facilitate bending motion; and
at least one force-generating actuators for manipulating the tubular elastic or superelastic element in bending motion away from the axis, the at least one force-generating actuators being attached to and located with said element.

26. The micromanipulator of claim 25, wherein the at least one actuators are selected from the group consisting of Shape Memory Alloy (SMA) actuators, piezoelectric actuators, and electro-active polymer actuators.

27. The micromanipulator of claim 26, wherein the at least one actuators are characterized as wires connected to an external apparatus and actuated remotely via the external apparatus.

28. An intravascular system comprising:
a micromanipulator having no mechanical joints, comprising a tubular structure having an axis and being made of an elastic or superelastic material; and
a plurality of compliant mechanisms spaced apart along the tubular structure, wherein each such mechanism is integrally formed from the tubular structure by removing material from the tubular structure to allow flexure of the mechanism; and
at least one force-generating actuators coupled to and located with at least one of the plurality of compliant mechanisms for effecting bending motions of the micromanipulator away from the axis.

29. The system of claim 28, wherein the at least one actuators are selected from the group consisting of Shape Memory Alloy (SMA) actuators, piezoelectric actuators, and electro-active polymer actuators.

30. The system of claim 28, wherein the at least one actuators are characterized as wires connected to an external apparatus and actuated remotely via the external apparatus.

31. The system of claim 28, further comprising:
two additional actuators configured to actuate the compliant apparatus in an orthogonal direction, enabling the micromanipulator with full three dimensional steering motions.

32. The system of claim 28, wherein the at least one actuators and the two additional actuators are characterized as SMA wires or SMA springs.

33. The system of claim 28, wherein
each compliant mechanism is individually controllable via the at least one actuators.

34. The system of claim 28, wherein
the at least one actuators are controlled by a remote electronic circuitry via a user interface.

35. The system of claim 28, wherein
the micromanipulator and the plurality of compliant mechanisms are assembled together subsequent to being respectively formed.

36. The system of claim 28, further comprising:
an ultrasound transducer coupled to the micromanipulator.

37. The system of claim 28, further comprising:
a cooling system coupled to the micromanipulator for regulating temperature thereof.

38. The system of claim 37, wherein
the cooling system comprises a pump and biocompatible cooling fluid; and wherein
the pump provides a constant flow of the cooling fluid to the micromanipulator to prevent the at least one actuators from overheating.

39. The apparatus of claim 1, further comprising at least one therapeutic interventional device, wherein said device is selected from the group consisting of a laser, a rotor blade device, a guidewire, a radio frequency device, a microwave device, a therapeutic ultrasound device, and a chemical delivery device.

40. The system of claim 17, further comprising at least one therapeutic interventional device, wherein said device is selected from the group consisting of a laser, a rotor blade device, a radio frequency device, a guidewire, a microwave device, a therapeutic ultrasound device, and a chemical delivery device.

41. The apparatus of claim 1, wherein said compliant mechanism exhibits a peak strain of less than 4%.

42. The apparatus of claim 1, wherein said compliant mechanism comprises a double helix configuration.

43. The apparatus of claim 1, wherein said compliant mechanism is formed by a process that produces a feature size of less than 200 μm.

44. The system of claim 17, wherein said compliant mechanism exhibits a peak strain of less than 4%.

45. The system of claim 17, wherein said compliant mechanism comprises a double helix configuration.

46. The system of claim 17, wherein said compliant mechanism is formed by a process that produces a feature size of less than 200 μm.

47. The micromanipulator of claim 25, wherein the at least one actuators are located at least partially external to the tube.

48. The system of claim 28, wherein the at least one actuators are located at least partially external to the tubular structure.

* * * * *

UNITED STATES PATENT AND TRADEMARK OFFICE
CERTIFICATE OF CORRECTION

| | | |
|---|---|---|
| PATENT NO. | : 7,115,092 B2 | Page 1 of 1 |
| APPLICATION NO. | : 10/667230 | |
| DATED | : October 3, 2006 | |
| INVENTOR(S) | : Byong-Ho et al. | |

It is certified that error appears in the above-identified patent and that said Letters Patent is hereby corrected as shown below:

Col. 2, Line 35, Delete "(WUS)" and insert -- (IVUS) --, therefor.

Col. 9, Line 59, In Claim 21, delete "electroactive" and insert -- electro-active --, therefor Signed and Sealed this Twenty-seventh Day of March, 2007

JON W. DUDAS
*Director of the United States Patent and Trademark Office*